United States Patent
Ripin

(10) Patent No.: US 7,084,277 B2
(45) Date of Patent: Aug. 1, 2006

(54) 3-AMINO-PIPERIDINE DERIVATIVES AND METHODS OF MANUFACTURE

(75) Inventor: David H. B. Ripin, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 118 days.

(21) Appl. No.: 10/717,958

(22) Filed: Nov. 20, 2003

(65) Prior Publication Data

US 2004/0102627 A1 May 27, 2004

Related U.S. Application Data

(60) Provisional application No. 60/428,324, filed on Nov. 21, 2002.

(51) Int. Cl.
C07D 211/56 (2006.01)
C07D 211/60 (2006.01)

(52) U.S. Cl. ........................................ 546/244; 546/245
(58) Field of Classification Search ................. 546/244, 546/245
See application file for complete search history.

(56) References Cited

U.S. PATENT DOCUMENTS

| | | | |
|---|---|---|---|
| 3,119,742 A | 1/1964 | Helmlich et al. | 167/82 |
| 3,492,397 A | 1/1970 | Peters et al. | 424/20 |
| 3,538,214 A | 11/1970 | Polli et al. | 424/19 |
| 4,060,598 A | 11/1977 | Groppenbacher et al. | 424/33 |
| 4,173,626 A | 11/1979 | Dempski et al. | 424/19 |
| 4,725,599 A | 2/1988 | Glazer et al. | 514/258 |
| 4,977,159 A | 12/1990 | Sevrin et al. | 514/292 |
| 5,559,128 A | 9/1996 | Chakravarty et al. | 514/323 |
| 2001/0053782 A1 | 12/2001 | Blumenkopf et al. | |

FOREIGN PATENT DOCUMENTS

| | | |
|---|---|---|
| EP | 0111864 | 6/1984 |
| EP | 0302788 | 2/1992 |
| EP | 0478363 | 4/1992 |
| EP | 0618196 | 10/1994 |
| WO | WO 9824446 | 6/1998 |
| WO | WO 9900368 | 1/1999 |
| WO | WO 9914214 | 3/1999 |
| WO | WO 0170673 | 9/2001 |
| WO | WO 0181347 | 11/2001 |
| WO | WO 0257244 | 7/2002 |

OTHER PUBLICATIONS

Duhamel, et al., "Synthesis of Bicyclic Aza–enones via a Lewis Acid Catalysed Michael–type Addition with Silyl Enol Ethers bearing a Nitrogen Atom.", Tetrahedron Letters, vol. 34, No. 24, pp. 3863–3866, 1993.
Kobayashi Osamu, Patent Abstracts of Japan, Publication No. 2002201192, Published Jul. 16, 2002.
Iwasaki Fumiaki, Patent Abstracts of Japan, Publication No. 11158147, Published Jun. 15, 1999.

Iorio, M.A., et al., "Synthesis and Conformational Study of Some Diastereoisomeric 4–Methyl–3–Phenyl–3–Piperidinols and Related Esters," Tetrahedron 1970, 26, 5519–5527.
Fukuyama, T., et al., "2– and 4–Nitrobenzenesulfonamides: Exceptionally Versatile Means for Preparation of Secondary Amines and Protection of Amines," Tetrahedron Lett. 1995, 36, 6373–6374.
Knight, D.W., et al., "β–Hydroxypiperidinecarboxylates: additions to the chiral pool from bakers' yeast reductions of β–keotpiperidinecarboxylates," J. Chem. Soc. Perkin Trans. 1 1998, 22, 3673–3684.
Shono, T., et al., "Acetoxylation of Piperdine Derivatives at the 3–Position Stereoselective Synthesis of Pseudoconhydrine andN–Methylpseudoconhydrine," Chem. Lett. 1984, 1101–1104.
Shono, T., et al., "Electroorganic Chemistry. 99. β–Acetoxylation and β–Halogenation of N–Methoxycarbonyl Cyclic Amines," J. Org. Chem. 1987, 52, 536–541.
Shono, T., et al., "Electroorganic Chemistry. 60. "Electroorganic Synthesis of Enamides and Enecarbamates and Their Utilization in Organic Synthesis, J. Am. Chem. Soc. 1982, 104, 6697–6703.
Shono, T., et al., "Anodic Oxidation of N–carbomethoxypyrrolidine: 2–Methoxy–N–Carbomethoxypyrrolidine," Org. Synth. 1985, 63, 206–213.
Matsumura, Y., et al., "A Convenient Method for Introducing Oxo Group into the β–Position of Cyclic Amines and Its Application to Synthesis of δ– Aminolevulinic Acid", Bull. Chem. Soc. Jpn. 1994, 67, 304–306.
Scully Jr., F.E., "Regioselective 2–Alkylation and 2–Arylation of Piperidine and Pyrrolidine via Organolithiation of Cyclic Imines," J. Org. Chem. Soc. 1980, 45, 1515–1517.

(Continued)

Primary Examiner—Taofiq Solola
(74) Attorney, Agent, or Firm—Gregg C. Benson; Christopher J. Verni

(57) ABSTRACT

This invention relates to 3-amino piperidine derivatives, their intermediates and methods of manufacture. As such, the present invention includes methods of making a compound of the formulas (Ia) and (Ib)

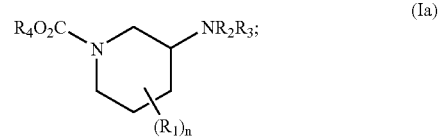

(Ia)

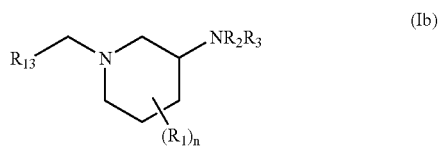

(Ib)

wherein $R_1$, $R_2$, $R_3$, $R_4$, $R_{14}$, and n are herein defined. The present invention also relates to the compounds used in such processes, as well as the compounds made by the processes.

15 Claims, No Drawings

OTHER PUBLICATIONS

Scully Jr., F.E., et al, "Superoxide in Organic Synthesis: A New Mild Method for the Oxidation of Amines to Carbonyls via N–Chloramines," *J. Org. Chem. Soc.* 1978, 43, 1467–1468.

Quick, J., et al., "A Convenient Synthesis of Pelletierine (2–Piperidylpropanone)," *Synthesis* 1976, 745–746.

Moon, M.W., et al,"Dopaminergic and Serotonergic Activities of Imidazoquinolinones and Related Compounds," *J. Med. Chem.* 1992, 35, 1076–1092.

Reitsema, R.H., et al., "Syntheses of 3–Aminopiperidines," *J. Am. Chem. Soc.* 1949, 71, 1680–1682.

Ebnoether, A., et al., *Helv. Chim. Acta* 1959, 42, 918–955.

Biel, J.H., et al., "Aminolysis and Hydrazinolysis Products of N–Methyl–3–chloropiperidine. Non–mercurial Diuretic Agents," *J. Am. Chem. Soc.* 1959, 81, 2527–2532.

Cooper, G.H., et al., "Synthesis of 5–Acetamido–2–acetylpiperidine," *J. Chem. Soc. C* 1971, 772–7.

Crider, A.M., et al., "Synthesis of Nitrosourea Derivatives of Pyridine and Piperidine as Potential Anticancer Agents," *J. Med. Chem.* 1980, 23, 848–851.

Armour, D.R., et al., "Tetrazole NK1 Receptor Antagonists: The Identification of an Exceptionally Potent Orally Active Antiemetic Compound" *Bioorg. Med. Chem. Lett.* 1996, 6, 1015–1020.

Nienburg, H., "3–amino–piperidin," *Chem. Ber.* 1937, 70, 635–638.

Glennon, R.A., et al., "2,3–Dihydro and Carbocyclic Analogues of Tryptamines: Interaction with Serotonin Receptors," *J. Med. Chem.* 1982, 25, 68–70.

Ripin, David H.B., et al., "Development of a scaleable route for the production of cis–N–benzyl–3–methylamino–4–methylpiperidine", *Org. Proc. Res. Dev.*, 7 (1), 115–120, 2003. 10.1021/op025599x S1083–6160(02)05599–8; Web Release Date: Dec. 2, 2002.

3-AMINO-PIPERIDINE DERIVATIVES AND METHODS OF MANUFACTURE

RELATED APPLICATION

The present application claims priority to U.S. patent application Ser. No. 60/428,324, filed Nov. 21, 2002, which is incorporated herein in its entirety.

FIELD OF THE INVENTION

This invention relates to 3-amino-piperadine derivatives, their intermediates, and methods of manufacture.

BACKGROUND

Pyrrolo[2,3-d]pyrimidine compounds are inhibitors of protein kinases, such as the enzyme Janus Kinase 3 (JAK3) and are therefore useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable. The pyrrolo[2,3-d]pyrimidine compounds, pharmaceutical compositions thereof and methods of use are described in co-pending application Ser. No. 09/732,669, filed Dec. 8, 2000, and assigned to the assignee of the present invention, which is incorporated herein by reference for all purposes.

SUMMARY OF THE INVENTION

As embodied and broadly described herein, this invention, in one aspect, relates to methods of making compounds of the formula (Ia)

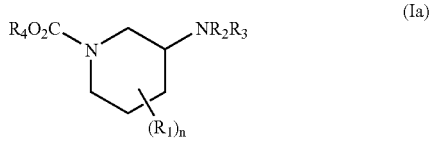

(Ia)

wherein $R_1$ is carboxy, cyano, deuterium, $(C_1-C_6)$alkyl, $(C_1-C_6)$alkoxy, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, $(C_1-C_6)$alkoxy$(C_1-C_6)$alkyl, $(C_1-C_6)$ acyloxy$(C_1-C_6)$alkyl, nitro, cyano$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1C_6)$acyl, $((C_1-C_6)$alkyl$)_2$amino$(C_1-C_6)$acyl, $R_{15}R_{16}N$—CO—O—, $R_{15}R_{16}N$—CO—$(C_1-C_6)$alkyl, $(C_1-C_6)$alkyl-S(O)$_m$, $R_{15}R_{16}NS(O)_m$, $R_{15}R_{16}NS(O)_m$ $(C_1-C_6)$alkyl, $R_{15}S(O)_m$ $R_{16}N$, $R_{15}S(O)_m R_{16}N(C_1-C_6)$alkyl or a group of the formula (VII):

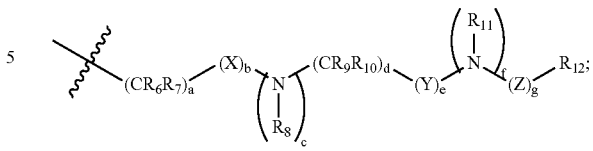

(VII)

$R_2$ is hydrogen, $(C_1-C_6)$alkyl, $(C_1-C_6)$alkylsulfonyl, $(C_2-C_6)$alkenyl, or $(C_2-C_6)$alkynyl wherein the alkyl, alkenyl and alkynyl groups are optionally substituted by deuterium, hydroxy, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R_2$ is $(C_3-C_{10})$cycloalkyl wherein the cycloalkyl group is optionally substituted by deuterium, hydroxy, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R_3$ is hydrogen, $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, halogen, trifluoromethyl, $(C_1-C_4)$alkoxy, $(C_1-C_6)$acyloxy, $(C_1-C_6)$alkylamino, $(C_1-C_6)$acylamino, $((C_1-C_6)$alkyl$)_2$amino, $(C_2-C_6)$alkenyl, $(C_2-C_6)$alkynyl, cyano, cyano$(C_1-C_6)$alkyl, trifluoromethyl$(C_1-C_6)$alkyl, nitro, or nitro$(C_1-C_6)$alkyl;

$R_4$ is $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, halogen, amino, trifluoromethyl, $(C_1-C_4)$alkoxy, $(C_1-C_6)$acyloxy, $(C_1-C_6)$alkylamino, $(C_1-C_6)$acylamino, $((C_1-C_6)$alkyl$)_2$amino, $(C_2-C_6)$alkenyl, $(C_2-C_6)$alkynyl, cyano, cyano$(C_1-C_6)$alkyl, trifluoromethyl$(C_1-C_6)$alkyl, nitro, or nitro$(C_1-C_6)$alkyl;

$R_6$, $R_7$, $R_8$, $R_9$, $R_{10}$ and $R_{11}$ are each independently hydrogen or $(C_1-C_6)$alkyl optionally substituted by deuterium, hydroxy, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino; $R_{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, $(C_1-C_6)$acyl, $(C_1-C_6)$alkylamino, $((C_1-C_6)$alkyl$)_2$ amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy $(C_1-C_6)$acylamino, amino$(C_1-C_6)$acyl, amino$(C_1-C_6)$acyl $(C_1-C_6)$alkyl, $(C_1-C_6)$alkylamino$(C_1-C_6)$acyl, $((C_1-C_6)$alkyl$)_2$amino$(C_1-C_6)$acyl, $R_{15}R_{16}N$—CO—O—, $R_{15}R_{16}N$—CO—$(C_1-C_6)$alkyl, $R_{15}C(O)NH$, $R_{15}OC(O)NH$, $R_{15}NHC(O)NH$, $(C_1-C_6)$alkyl-S(O)$_m$, $(C_1-C_6)$alkyl-S(O)$_m$—$(C_1-C_6)$alkyl, $R_{15}R_{16}NS(O)_m$, $R_{15}R_{16}NS(O)_m$ $(C_1-C_6)$alkyl, $R_{15}S(O)_m$ $R_{16}N$, or $R_{15}S(O)_m R_{16}N(C_1-C_6)$alkyl;

$R_{15}$ and $R_{16}$ are each independently hydrogen or $(C_1-C_6)$ alkyl;

X is $S(O)_p$, oxygen, carbonyl or —C(=N-cyano)-;

Y is $S(O)_p$ or carbonyl;

Z is $S(O)_p$, carbonyl, C(O)O—, or C(O)NR—;

a is 0, 1, 2, 3 or 4;

b, c, e, f and g are each independently 0 or 1;

d is 0, 1, 2, or 3; m is 0, 1 or 2; n is 1, 2, 3, or 4; p is 0, 1 or 2; and wherein the method comprises reacting $NHR_2R_3$, $N(CH_3)R_2H$, or $N(CH_2CH_3)R_2H$ with a compound of formula (IIa):

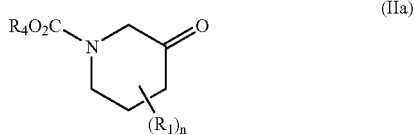

and reducing the compound so formed with a reducing agent. In one embodiment, the reducing agent is a borohydride.

Moreover, the present invention relates to formation of the compound of the formula (IIa) by reacting a compound having the formula $R_4OH$, water, or $R_4NH_2$ and a compound of the formula (IIIa):

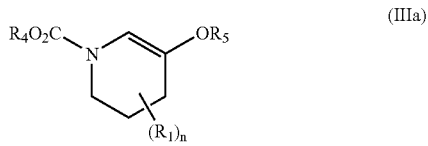

wherein $R_5$ is $CO(C_1-C_6)$alkyl.

The present invention further relates to formation of the compound of the formula (IIa) by heating a compound having the formula (IVa):

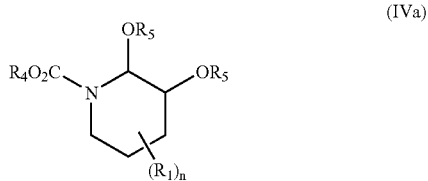

with a compound having the formula $(C_1-C_6)$alkyl-(C=O)—O—(C=O)—$(C_1-C_6)$alkyl.

In addition, the present invention relates to formation of the compound of the formula (IVa) by oxidizing a compound having the formula (Va):

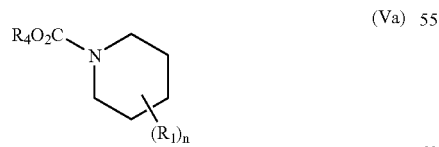

under oxidizing conditions. In one embodiment, the oxidizing conditions are an electrochemical oxidation.

The present invention also relates to formation of the compound of the formula (Va) by reacting a compound having the formula $WCO_2R_4$ and a compound having the formula (VIa):

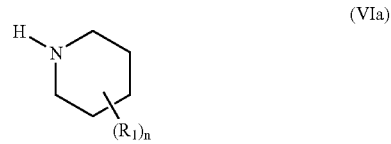

wherein W is halogen.

A second aspect of the present invention relates to methods of making a compound having the formula (Ib):

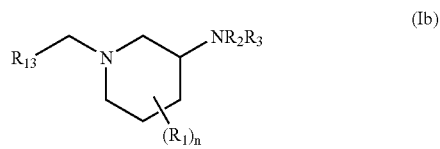

wherein $R_{13}$ is $(C_2-C_6)$alkenyl, $(C_2-C_6)$alkynyl, $(C_6-C_{10})$aryl, $(C_1-C_6)$carboalkoxy, $(C_5-C_9)$heteroaryl, $(C_6-C_{10})$aryl$(C_1-C_6)$alkyl, or $(C_5-C_9)$heteroaryl$(C_1-C_6)$alkyl wherein the $R_{13}$ group is optionally substituted by deuterium, hydroxy, amino, trifluoromethyl, $(C_1-C_6)$alkyl, $(C_1-C_4)$alkoxy, $(C_1-C_6)$alkylamino, $((C_1-C_6)$alkyl$)_2$amino, $(C_2-C_6)$alkenyl, $(C_2-C_6)$alkynyl, trifluoromethyl$(C_1-C_6)$alkyl, nitro, or nitro$(C_1-C_6)$; and wherein the method comprises reducing a compound of formula (IIb):

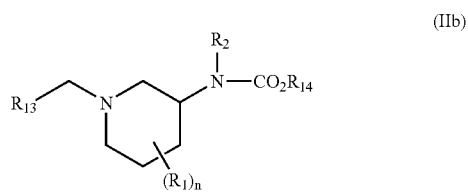

with a reducing agent, wherein $R_{14}$ is $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, halogen, amino, trifluoromethyl, $(C_1-C_4)$alkoxy, $(C_1-C_6)$alkylamino, $((C_1-C_6)$alkyl$)_2$amino, $(C_2-C_6)$alkenyl, $(C_2-C_6)$alkynyl, trifluoromethyl$(C_1-C_6)$alkyl, nitro, or nitro$(C_1-C_6)$alkyl., The present invention also relates to formation of the compound of the formula (IIb) by reacting a compound having the formula (IIIb):

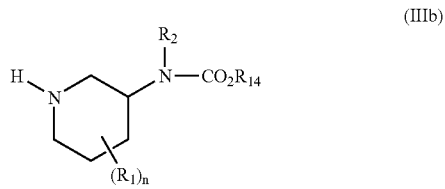

with an aldehyde of formula $R_{13}$—(C=O)—H and reducing the compound so formed with a reducing agent. In one embodiment, the reducing agent is lithium aluminum hydride.

Moreover, the present invention relates to formation of the compound of the formula (IIIb) by hydrogenating a compound having the formula (IVb):

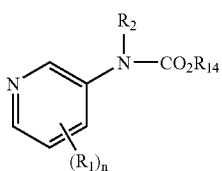

(IVb)

in the presence of a catalyst. In one embodiment, the catalyst is Rh/alumina or Rh/C.

The present invention also relates to formation of the compound of the formula (IVb) by reacting a compound having the formula (Vb):

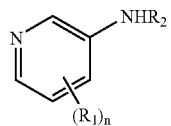

(Vb)

with $(R_{14}-O-(C=O))_2O$ or $R_{14}-O-(C=O)-X$ wherein X is halo.

Furthermore, in additional aspects, the present invention relates to the compounds herein described including compounds of the formula (Ia), (Ib) and (IIb).

In some preferred embodiments of the methods and compounds of aforementioned aspects of the present invention, $R_1$ is $(C_1-C_6)$alkyl and n is one; $R_2$ and $R_3$ are each hydrogen or $(C_1-C_6)$alkyl; $R_4$ is $(C_1-C_6)$alkyl; and/or $R_{13}$ is $(C_6-C_{10})$aryl.

In one embodiment, the compound of formula (Ia) has the relative stereochemistry of formula (Ia-1):

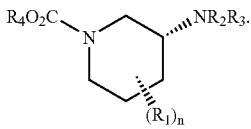

(Ia-1)

In another embodiment, the compound of formula (Ib) has the relative stereochemistry of formula (Ib-1):

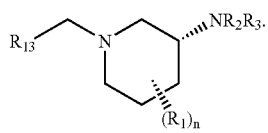

(Ib-1)

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

Before the present compounds and methods are disclosed and described, it is to be understood that this invention is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" and "halide" includes fluorine, chlorine, bromine, and iodine.

"$(C_3-C_{10})$cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"$(C_2-C_9)$heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said $(C_2-C_9)$heterocycloalkyl rings is through a carbon or a Sp3 hybridized nitrogen heteroatom.

"$(C_2-C_9)$heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said $(C_2-C_9)$heterocycloalkyl rings is through a carbon atom or a $sp^3$ hybridized nitrogen heteroatom.

"Aryl" when used herein refers to phenyl or naphthyl.

By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The term "subject" is meant an individual. Preferably, the subject is a mammal such as a primate, and more preferably, a human. Thus, the "subject" can include domesticated animals, livestock, and laboratory animals.

In general, "effective amount" or "effective dose" means the amount needed to achieve the desired result or results (treating or preventing the condition). One of ordinary skill in the art will recognize that the potency and, therefore, an "effective amount" can vary for the various compounds used in the invention. One skilled in the art can readily assess the potency of the compounds.

Unless otherwise noted, numerical values described and claimed herein are approximate. Variation within the values may be attributed to equipment calibration, equipment errors, purity of the materials, among other factors. Additionally, variation may be possible, while still obtaining the same result.

The following reaction Schemes illustrate the preparation of the compounds of the present invention. Unless otherwise indicated the substituents in the reaction Schemes and the discussion that follow are defined as above.

SCHEME 1

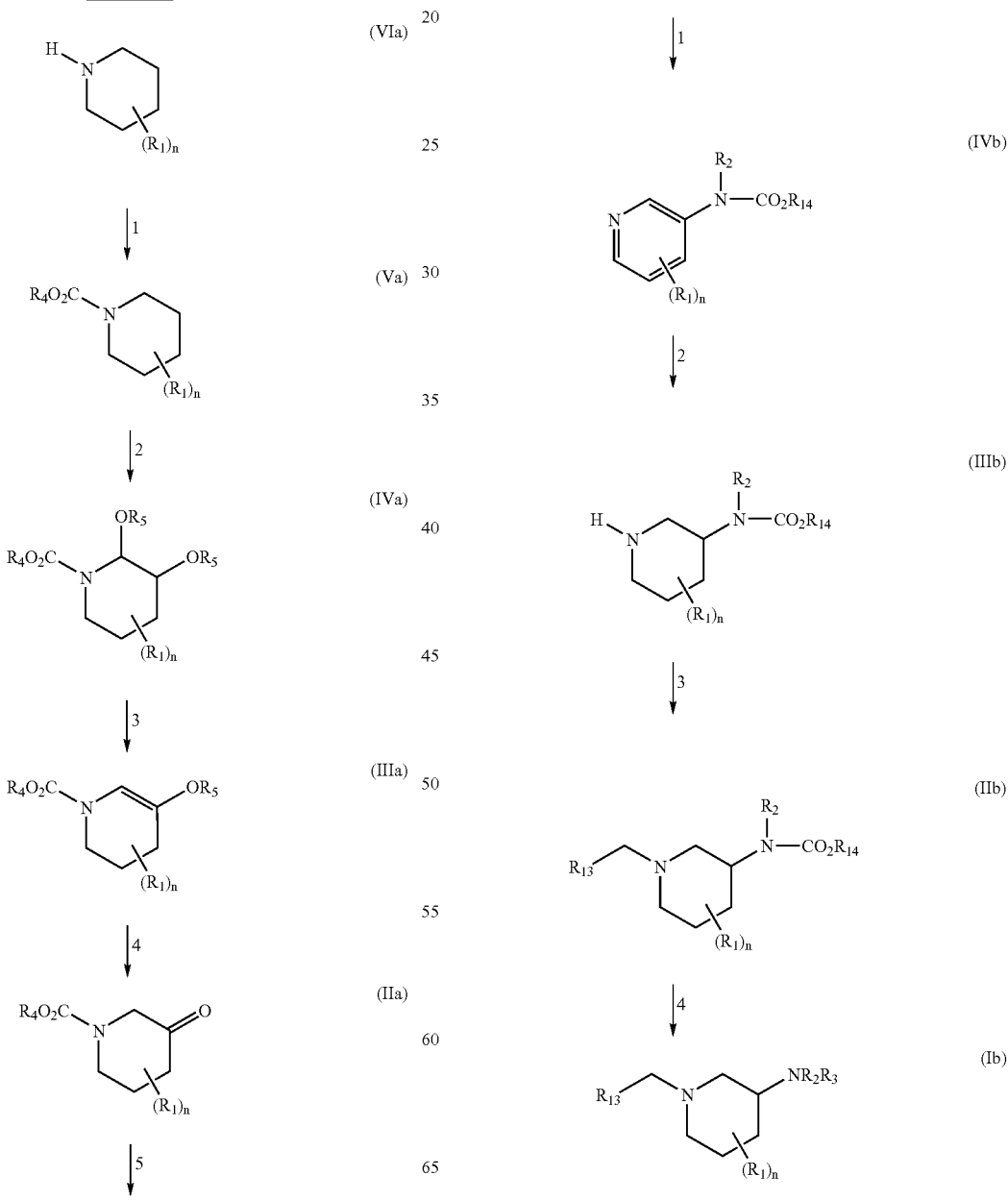

SCHEME 2

SCHEME 3

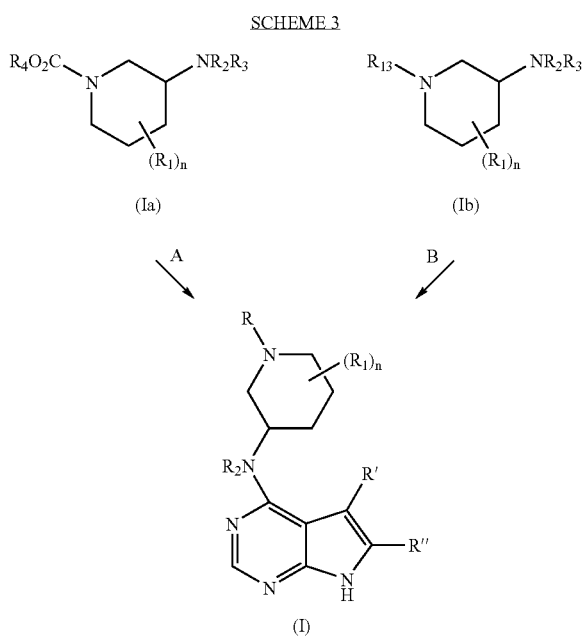

In step 1 of Scheme 1, the compound of formula (VIa) is converted to the carbamate of formula (Va) by reaction with a compound of formula W—$CO_2R_4$ in a solvent system. The solvent system preferably contains an amine, such as triethylamine, diisopropylethylamine, or other tertiary amine. Other solvents may also be used, including dichloromethane, tetrahydrofuran, and methyltetrahydrofuran. The mixture is then cooled to approximately −80° to 25° C. and the W—$CO_2R_4$ is slowly added to control the temperature. The mixture is allowed to stir until for at least one hour, preferably, four hours or more.

In step 2 of Scheme 1, the carbamate of formula (Va) is oxidized to form the oxidation product (IVa). Typically, the oxidation reaction produces a mixture of compounds having the formula (IVa). Any suitable oxidation conditions may be used. Preferred conditions include electrochemical oxidation, such as performing the oxidation reaction in an electrolytic solution in an electric cell and electrolyzing the cell. In one embodiment, the electrolytic solution is a mixture of acetic acid and potassium acetate. In another embodiment, the electrolytic solution includes acetic anhydride. The cathode and anode may be made of any suitable material, including platinum and niobium. The mixture is then electrolyzed at an appropriate current until the reaction is substantially complete. The temperature of the electrolytic solution may be maintained at a temperature lower than 60° C., preferably lower than 40° C.

The oxidation product (IVa) is heated in step 3 of Scheme 1 with a compound having the formula ($C_1$–$C_6$)alkyl-(C=O)—O—(C=O)—($C_1$–$C_6$)alkyl, including acetic anhydride, to produce the enamino acetate of formula (IIa). The temperature is preferably maintained at about 60° C. to about 160° C.; more preferably, the temperature is raised to about >100° C., more preferably to about >120° C. The mixture is allowed to stir for at least two hours, preferably 4 hours or more.

In step 4 of Scheme 1, the enamino acetate (IIIa) is converted to the ketopiperidine (IIa) by reaction with a compound having the formula $R_4OH$, water or $R_4NH_2$. Preferably, this reaction is maintained at temperatures less than 20° C., more preferably less than 5° c.

In step 5 of Scheme 1, the ketopiperidine (IIa) is converted to the aminopiperidine (Ia) by reaction with $NHR_2R_3$, $N(CH_3)R_2R_3$, or $N(CH_2CH_3)R_2R_3$. The product of this reaction is reduced with a reducing agent to form the aminopiperidine (Ia). The reactions are typically conducted in a solvent, such as methanol, at ambient temperature for a time period between about 12 hours to about 18 hours. Exemplary reducing agents include borohydrides, such as sodium cyanoborohydride and sodium borohydride.

In step 1 of Scheme 2, the carbamate (IVb) is formed by reacting the compound of formula (Vb) with a compound of the formula ($R_{14}$—O—(C=O))$_2$O or $R_{14}$—O—(C=O)—X wherein X is halo. Preferably, the temperature is maintained below 0° C. The reaction is substantially complete within minutes, usually within at least an hour.

In step 2 of Scheme 2, the carbamate (IVb) is hydrogenated to form the compound of formula (IIIb). The hydrogenation also may lead to cis-trans isomers. Certain catalysts may be desired for the cis:trans selectivity. Exemplary hydrogentation catalysts include $PtO_2$, Rh/C (several types), $RuO_2$, Rh/$Al_2O_3$, Ru/C (several types), Lindlar's catalyst, and Wilkinson's catalyst. Exemplary solvents include acetic acid, propanol, ethanol, methanol/ammonium hydroxide, acetonitrile, tetrahydrofuran, cyclohexane, heptanes, toluene, dimethylformamide, water. Generally, the temperature of the reaction is maintained above room temperature, preferably above 60 C, and the pressure is increased above atmospheric pressure with hydrogen gas.

In step 3 of Scheme 2, the compound of formula (IIIb) is reacted with an aldehyde of formula $R_{13}$—(C=O)—H and reduced with a reducing agent to form the compound (IIb). The reactions are typically conducted in a solvent, such as methanol, at ambient temperature for a time period between about 12 hours to about 18 hours. Exemplary reducing agents include borohydrides, such as sodium cyanoborohydride and sodium borohydride. In one embodiment, the reducing agent is triacetoxyborohydride.

Finally, in step 4 of Scheme 2, the compound of formula (IIb) is reduced to the compound of formula (Ib). Exemplary reducing agents include lithium aluminum hydride, Vitride (Red-Al), and borane. The reduction is carried out in a solvent such as tetrahydrofuran, diethylether, or methyltetrahydrofuran, preferably at temperatures of about −10° to about 100° C. for about five minutes to about 48 hours.

In reactions A and B of Scheme 3, the compound of formula (Ia) or (Ib) as appropriate is coupled with a 4-chloro-pyrrolo[2,3-d]pyrimidine compound of the formula (A):

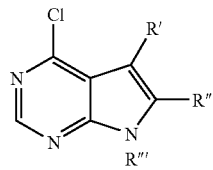

wherein R' and R" are each independently selected from the group consisting of hydrogen, deuterium, amino, halo, hydoxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$) alkoxy, ($C_3$–$C_{10}$)cycloalkyl wherein the alkyl, alkoxy or cycloalkyl groups are optionally substittued by one to three groups selected from halo, hydroxy, carboxy, amino ($C_1$–$C_6$) alkylthio, ($C_1$–$C_6$)alkylamino, (($C_1$–$C_6$)alkyl)$_2$amino, ($C_5$–$C_9$)heteroaryl, ($C_2$–$C_9$)heterocycloalkyl, ($C_3$–$C_9$) cycloalkyl or ($C_6$–$C_{10}$)aryl; or $R^2$ and $R^3$ are each independently ($C_3$–$C_{10}$)cycloalkyl, ($C_3$–$C_{10}$)cycloalkoxy, ($C_1$–$C_6$) alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$) arylsulfonyl, ($C_1$–$C_6$)acyl, ($C_1$–$C_6$)alkoxy-CO—NH—, ($C_1$–$C_6$)alkyamino-CO—, ($C_5$–$C_9$)heteroaryl, ($C_2$–$C_9$) heterocycloalkyl or ($C_6$–$C_{10}$)aryl wherein the heteroaryl, heterocycloalkyl and aryl groups are optionally substituted by one to three halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$) alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$)alkoxycarbonyl ($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$) alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkoxy)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$) alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_5$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$) alkyl)$_2$amino-CO—NH—($C_1$–$C_6$)alkyl, ($C_6$–$C_{10}$) arylamino-CO—NH—($C_1$–$C_6$)alkyl, ($C_5$–$C_9$) heteroarylamino-CO—NH—($C_1$–$C_6$)alkyl, ($C_1$–$C_6$) alkylsulfonyl, ($C_1$–$C_6$)alkylsulfonylamino, ($C_1$–$C_6$) alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino ($C_1$–$C_6$)alkyl, ($C_1$–$C_6$)alkylsulfonylamino, ($C_1$–$C_6$) alkylsulfonylamino($C_1$–$C_6$)alkyl, ($C_5$–$C_9$)heteroaryl and ($C_2$–$C_9$)heterocycloalkyl; and R''' is hydrogen or a protecting group;

to create the 4-aminopyrrolo[2,3-d]pyrimidine compound of formula (I), wherein R is $R_4$—O—(C=O)— or $R_{13}$—($CH_2$)—.

The coupling reaction is carried out in an alcohol solvent, such as tert-butanol, methanol or ethanol, or other high boiling organic solvents, such as dimethylformamide, triethylamine, 1,4-dioxane or 1,2-dichloroethane, at a temperature between about 60° C. to about 120° C., preferably about 80° C. Typical reaction times are between about 2 hours to about 48 hours, preferably about 16 hours.

If R''' is a protecting group, the protecting group may be removed in an additional step. For example, removal of the protecting group, wherein R''' is benzenesulfonyl, is carried out by treating the product of the coupling reaction A or B with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group, wherein R is benzyl, is conducted by treating the product of the coupling reaction A or B with sodium in amrionia at a temperature of about −78° C. for a time period between about 15 minutes to about 1 hour.

Unless indicated otherwise, the pressure of each of the above reactions is not critical. Generally, the reactions are conducted at a pressure of about one to about three atmospheres, preferably at ambient pressure (about one atmosphere).

The compounds of the formulas (Ia) and (Ib) are capable of forming a wide variety of different salts with various inorganic and organic acids.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as acetone, methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the calcium, sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are important in the manufacture of compound of the formula I (wherein the substituents are as previously defined):

(I)

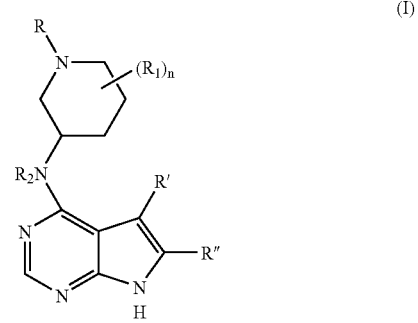

The compounds of the formula I and its pharmaceutically acceptable salts (hereinafter also referred to, collectively, as "the active compounds") are inhibitors of protein kinases, such as the enzyme Janus Kinase 3 (JAK3) and are therefore useful therapy as immunosuppressive agents for treating or preventing organ transplant rejection, xeno transplation; lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, leukemia and other autoimmune diseases, acute and chronic organ transplant rejection, heart transplant rejection, lung transplant rejection, liver transplant rejection, kidney transplant rejection, pancreas transplant rejection, uterus transplant rejection, joints transplant rejection, islets transplant rejection, bone marrow transplant rejection, limb transplant rejection, cornea transplant rejection, skin transplant rejection, hepatocytes transplant rejection, hepatocytes cell transplant rejection, pancreatic beta-cells transplant rejection, stem cell transplant rejection, neural cell transplant rejection, cardiac myocytes cell transplant rejection, immune-related infertility, HIV replication suppression, Hepatitis B, Hepatitis C, interstitial cystitis, primary biliary cirrhosis, psoriasis, psoriatic arthritis, and juvenile arthritis in a mammal, including a human, The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray:presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., asthma) in the average adult human are preferably arranged so that each metered dose or "puff" of aerosol contains 20 μg to 1000 μg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active compounds of formula (Ia-1) administered in a pharmaceutically acceptable form either alone or in combination with one or more additional agents which modulate a mammlian immune system or with antiinflammatory agents, agents which may include but are not limited to cyclosporin A (e.g. Sandimmune® or Neoral®, rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acctaminophen, ibuprofen, naproxen, piroxicam, and antiinflmmatory steroids (e.g. prednisolone or dexamethasone), an EPO, FK 778, Sdz-rad, steroids, IVIG, COX-2 inhibitor, NSAIDS, FTY720, basiliximab, donor cells, enerolimus, anti-CD28/CTLA41g, ISTA-TX-247, gancyciovir, interferon and alpha/rebif, septra, anti-TNFS, P38 inhibitors, $CCR_1$ antagonists, PDE4 antagonists, lipitor/statins, acyclovir, ribovikin, protease inhibitors/RTIs, insulin, rituximab, cetirizine or H1 blockers; and such agents may be administered as part of the same or separate dosage forms, via the same or different routes of administration, and on the same or different administration schedules according to standard pharmaceutical practice.

FK506 (Tacrolimus) is given orally at 0.10–0.15 mg/kg body weight, every 12 hours, within first 48 hours postoperative. Dose is monitored by serum Tacrolimus trough levels.

Cyclosporin A (Sandimmune oral or intravenous formulation, or Neoral®, oral solution or capsules) is given orally at 5 mg/kg body weight, every 12 hours within 48 hours postoperative. Dose is monitored by blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

Biological Assay

JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog # P0275), coated onto Nunc Maxi Sorp plates at 100 μg/ml overnight at 37° C. The morning after coating, the plates are washed three times and JAK3 is added to the wells containing 100 μl of kinase buffer (50 mM HEPES, pH 7.3, 125 mM NaCl, 24 mM MgC12)+0.2 uM ATP+1 mM Na orthovanadate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

Inhibition of Human IL-2 Dependent T-Cell Blast Proliferation

This screen measures the inhibitory effect of compounds on IL-2 dependent T-Cell blast proliferation in vitro. Since signaling through the IL-2 receptor requires JAK-3, cell active inhibitors of JAK-3 should inhibit IL-2 dependent T-Cell blast proliferation.

The cells for this assay are isolated from fresh human blood. After separation of the mononuclear cells using Accuspin System-Histopaque-1077 (Sigma # A7054), primary human T-Cells are isolated by negative selection using Lympho-Kwik T (One Lambda, Inc., Cat # LK-50T). T-Cells are cultured at 1–2×10$^6$/ml in Media (RPMI+10% heat-inactivated fetal calf serum (Hyclone Cat # A-1111-L)+1% Penicillin/Streptomycin (Gibco)) and induce to proliferate by the addition of 10 ug/ml PHA (Murex Diagnostics, Cat # HA 16). After 3 days at 37° C. in 5% $CO_2$, cells are washed 3 times in Media, resuspended to a density of 1–2×10$^6$ cells/ml in Media plus 100 Units/ml of human recombinant IL-2 (R&D Systems, Cat # 202-IL). After 1 week the cells are IL-2 dependent and can be maintained for up to 3 weeks by feeding twice weekly with equal volumes of Media+100 Units/ml of IL-2.

To assay for a test compounds ability to inhibit IL-2 dependent T-Cell proliferation, IL-2 dependent cells are washed 3 times, resuspended in media and then plated (50,000 cells/well/0.1 ml) in a Flat-bottom 96-well micro-titerplate (Falcon # 353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% $CO_2$ for 72 hours. Plates are then pulsed with $^3$H-thymidine (0.5 uCi/well) (NEN Cat # NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An $IC_{50}$ value (uM) is determined from this plot.

Experimental

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in 0° C. or is at ambient temperature, and pressure is at or near atmospheric. Commercial reagents were utilized without further purification. The following abbreviations are herein used:

AA is amino acid
AcOH is acetic acid
Boc is t-butoxy carbonyl
$CDCl_3$ is deuteriotrichloromethane
DMF is N,N-dimethylformamide
EtOAc is ethyl acetate
HCl is hydrochloric acid
HMDS is hexamethyldisilazane
IPE is isopropyl ether
MeOH is methanol
THF is tetrahydrofuran
g is grams
L is liter
M is molar
ml is milliliter
mmol is millimole
MHz is mega hertz
N is normal
psi is pounds per square inch
h is hours
min is minutes
sec is seconds
mp is melting point
RT is room temperature
Vacuo is in vacuum
~ is roughly approximate to*
HPLC is high pressure liquid chromatography
LCMS is liquid chromatograph mass spectrometer
NMR is nuclear magnetic resonance
TLC is thin layer chromatography

* Note that all numbers provided herein are approximate, but effort have been made to ensure accuracy with respect to numbers (e.g., amounts, temperature, etc.); however some errors and deviations should be accounted for.

EXAMPLE 1

Cis-(1-Benzyl-4-methyl-piperidin-3-yl)-methyl-amine hydrochloride salt
(4-Methyl-pyridin-3-yl)-carbamic acid methyl ester The synthesis was carried out by charging 2 grams (1 equiv., 18.5 mmol) 4-Methyl-pyridin-3-ylamine to a solution of 6.55 grams potassium t-butoxide (3 equiv., 55.5 mmol) in 10 ml THF (6.66 euiv., 123 mmol) at 0° C. Upon anion formation, 2.34 ml dimethyl carbonate (1.5 equiv., 27.7 mmol) were charged to the reaction at a rate so that the temperature stayed below 0° C. The reaction was complete within 30 minutes and the red slurry was quenched with 50 ml water (25 volumes) and extracted in 50 ml ethyl acetate (25 volumes). The aqueous layer was extracted with 50 ml ethyl acetate (25 volumes) and then the orange organic layers were concentrated to an orange solid. NMR data showed that t-butanol existed in the product so the solids were slurried in 10 ml toluene (5 volumes) and then concentrated to dryness. This operation was performed three times in order to give very clean light orange solids. (89% yield). $^1$H NMR: δ8.90 (1 H, brs), 8.28 (1 H, d, J=4.8), 7.16–7.14 (1 H, m), 6.54 (1 H, brs), 3.80 (3 H, s), 2.29 (3 H, s).

Cis-(4-Methyl-piperidin-3-yl)-carbamic acid methyl ester

The hydrogenation was carried out by charging 5 grams (1 equiv., 30.1 mmol) (4-methyl-pyridin-3-yl)-carbamic acid methyl ester, 50 ml ethanol (10 volumes), and 2.5 grams rhodium on alumina (0.5 wt. equivs.) to a bomb hydrogenator. The hydrogenation was performed under 100 psi hydrogen at 100° C. for 24 hours to give only cis-(4-methyl-piperidin-3-yl)-carbamic acid methyl ester and its trans isomer (5:1 ratio) in quantitative yield. $^1$H NMR: δ5.6 (1 H, d, J=8.4 Hz), 3.66 (1 H, d, J=3.6 Hz), 3.65–3.57 (3 H, brs), 3.1 (2 H, d, J=9.6, minor isomer), 2.91–2.86 (2 H, m), 2.67–2.64 (1 H, m), 2.54–2.43 (1 H, m), 2.2–1.9 (1 H, m, minor isomer), 1.78–1.65 (5 H, brs, minor isomer), 1.65–1.59 (4 H, m, minor isomer), 1.36–1.25 (2 H, m), 1.24–1.13 (2 H, m), 0.92 (3 H, d, J=6.8 Hz, minor isomer), 0.83 (3 H, d, J=7.2).

Cis-(1-Benzyl-4-methyl-piperidin-3-yl)-carbamic acid methyl ester

The reductive amination of cis-(4-methyl-piperidin-3-yl)-carbamic acid methyl ester was carried out by charging 3.9 grams (1 equiv., 22.6 mmol) to 2.07 ml benzaldehyde (0.9 equiv., 20.4 mmol), 9.6 grams sodium triacetoxyborohydride (2 equivs., 45.3 mmol) and 39 ml methylene chloride (10 volumes). The reaction was stirred at 20° C. and was allowed to exotherm to 30°–35° C. The reaction was complete by GCMS within 30 minutes. The reaction was quenched with 78 ml saturated sodium bicarbonate (20 volumes), extracted into 78 ml methylene chloride (20 volumes) and concentrated to a clear oil. (70% yield). $^1$H NMR: δ7.2–7.3 (5 H, m, aromatic protons), 5.50–5.48 (1 H, d, J=8.8 Hz), 3.77–3.75 (1 H, d, J=8.0 Hz), 3.63 (3 H, s), 3.45–3.38 (2 H, m), 2.77–2.74 (2 H, d, J=11.2 Hz), 2.14–2.01 (1 H, m), 1.94–1.89 (1 H, m), 1.57–1.55 (1 H, brs), 1.37–1.20 (2 H, m), 0.876 (3 H, d, J=9.2 Hz).

(1-Benzyl-4-methyl-piperidin-3-yl)-methyl-amine

The reduction of cis-(1-benzyl-4-methyl-piperidin-3-yl)-carbamic acid methyl ester was performed by charging 2 grams substrate (1 equiv., 7.62 mmol) to a solution of 20 ml THF (10 volumes) and 15.2 ml 1 M LAH in THF (2 equiv., 15.2 mmol). The addition was performed at a rate so that the temperature reached 30°–40° C. and then the reaction was allowed to cool to 20° C. The reaction was worked up by quenching with 40 ml Rochelle Salt (20 volumes) to a temperature of 35° C. and then extracting the product 2 times into 20 ml methylene chloride (10 volumes). The filtrate was then concentrated to a clear and colorless oil. (90% yield). Note that the starting material needs to be clean in order for this reaction to proceed in high yield.

$^1$H NMR: δ7.2–7.3 (5 H, m, aromatic protons), 3.54–3.51 (1 H, d, J=13.6), 3.40–3.37 (1H, d, J=13.6), 2.70–2.62 (2 H, m), 2.39–2.36 (1 H, brs) 2.32 (3 H, s), 2.29–2.12 (1 H, brs), 2.1.0–2.00 (1 H, brs), 1.66 (1 H, brs), 1.47–1.43 (2 H, m), 1.32 (1 H, brs), 0.936–0.919 (3 H, d, J=6.8).

Cis-(1-Benzyl-4-methyl-piperidin-3-yl)-methyl-amine hydrochloride salt

The final salt formation was performed by charging 1.5 grams cis-(1-benzyl-4-methyl-piperidin-3-yl)-methyl-amine (1 equiv., 5.15 mmol) and 4.5 ml ethanol (3 volumes) to a reactor at 0° C. To the 0° C. pot, was charged 0.93 ml 36% HCl (0.625 volumes) so that the temperature stayed below 10° C. Next 3 mls ethanol (2 volumes) were concentrated from the reaction. To the reaction was charged 7.5 mls ethyl acetate (5 volumes), the reaction was stirred for 5 minutes and then 6 mls ethyl acetate (4 volumes) were removed in vacuo. 7.5 mls ethyl acetate (5 volumes) were again charged and the concentration was again performed. Next, 4.5 mls acetone (3 volumes) were added and the reaction was slowly cooled to 0° C. in order to afford white solids. (37.5% yield). $^1$H NMR: δ7.78–7.76 (2 H, d, J=8.0 Hz), 7.29–7.18 (5 H, m, aromatic protons), 5.55 (1 H, s), 3.45–3.41 (1 H, d, J=13.2 Hz), 3.39–3.36 (1 H, d, J=13.2 Hz), 2.79 (1 H, brs), 2.63 (1 H, brs), 2.45 (3 H, s), 2.30 (2 H, s), 2.25–2.05 (1H, m), 1.76 (1 H, brs), 1.40–1.39 (2 H, m), 0.875–0.845 (3 H, d, J=12).

EXAMPLE 2

4-Methyl-3-methylamino-piperidine-1-carboxylic acid methyl ester

4-Methyl-piperidine-1-carboxylic acid methyl ester

To a three neck round bottom flask was added 360 g of 4-methylpiperdine, 470 mL of triethylamine, and 390 mL of methylene chloride and the mixture was cooled in an ice bath. To this mixture was added methylchloroformate (260 mL) in methylene chloride (215 mL) slowly to maintain a reaction temperature of 20 C or below. The reaction was stirred overnight, then 200 mL of water was added and the layers were separated. The organic layer was washed with dilute HCl, satd. NaHCO$_3$, and brine, and then the organic layer was dried over sodium sulfate and the solvent was removed in vacuo. The product was distilled at 90–93 C at ~10 mm pressure to provide 338 g of product.

Mixture of 2,3-Diacetoxy-4-methyl-piperidine-1-carboxylic acid methyl ester and 3-Acetoxy-2-hydroxy-4-methyl-piperidine-1-carboxylic acid In a 500 mL undivided glass cell equipped with a 60 cm$^2$ Pt mesh anode and a Pt-clad Nb mesh cathode. A polypropylene mesh separator was placed between the electrodes. To the cell was charged 50 g of 4-Methyl-piperidine-1-carboxylic acid methyl ester, 40 g of KOAc, and 320 mL of HOAc. The mixture was electrolyzed at a constant current of 6.0A until 20 F/mol was passed through the mixture. The cell voltage varied between 13.5V and 20V. The reaction was immersed in a cold water bath to maintain the reaction temperature around 35–40 C. The crude mixture of 2,3-Diacetoxy-4-methyl-piperidine-1-carboxylic acid methyl ester and 3-Acetoxy-2-hydroxy-4-methyl-piperidine-1-carboxylic acid methyl ester was carried into the next step.

5-Acetoxy-4-methyl-3,4-dihydro-2H-pyridine-1-carboxylic acid methyl ester 101.9 g (0.649 mol) of the mixture of 2,3-diacetoxy-4-methyl-piperidine-1-carboxylic acid methyl ester and 3-acetoxy-2-hydroxy-4-methyl-piperidine-1-carboxylic acid, was concentrated under reduced pressure until a solid formed. The solid was then added to a 2 L round bottom flask equipped with a nitrogen outlet, condenser and thermocouple. To this mixture was added acetic anhydride (430 ml) and then refluxed at 141° C. for two hours. The solution was stirred overnight at room temperature. Most of the acetic anhydride was removed under reduced pressure and the remaining amount was removed by adding H$_2$O (400 ml) and a 5% solution of NaHCO$_3$ until the pH>7. The aqueous mixture was extracted with ethyl acetate (3×250 ml), the organic layers were combined and the ethyl acetate was removed under reduced pressure. Approximately 119.0 g of a thick brown oil material 5-acetoxy-4-methyl-3,4-dihydro-2H-pyridine-1-carboxylic acid methyl ester was recovered. The TLC indicates conversion to product 5-acetoxy-4-methyl-3,4-dihydro-2H-pyridine-1-carboxylic acid methyl ester as the major component. The material was split evenly into two portions for separate hydrolysis reactions.

4-Methyl-3-oxo-piperidine-1-carboxylic acid methyl ester (Hydrolysis Using Dimethylamine):

In a 1 L flask, 60 g of crude product 5-acetoxy-4-methyl-3,4-dihydro-2H-pyridine-1-carboxylic acid methyl ester was dissolved in 100 ml of MeOH and 40 g (0.325 mol) of 40% dimethylamine in methanol was added over 15 min at 0° C. The, mixture was left to stir under nitrogen at room temperature overnight. The TLC showed product 4-Methyl-3-oxo-piperidine-1-carboxylic acid methyl ester was formed as the major component. The methanol solution was removed under reduced pressure and the residue was extracted with dichloromethane (3×100 mL). The dichloromethane layer was washed with water (3×50 ml) and the organic layer was separated and the solvent removed under reduced pressure. The crude residue was purified by column chromatography.

The product was purified on silica gel column (360 g). Elution with hexane/ethyl acetate mixture 70:30 (5 L) furnished non-polar byproducts. Continued elution with the same solvent mixture (6 L) followed by hexane/ethyl acetate 50:50 (3 L) furnished compound 4-Methyl-3-oxo-piperidine-1-carboxylic acid methyl ester as an oil after the solvents were removed under vacuum. Yield: 11.9 g (0.0696 mol, 27%), TLC ($SiO_2$, ethyl acetate/hexane 1:1) and NMR.

4-Methyl-3-oxo-piperidine-1-carboxylic acid methyl ester (Synthesis with Sodium Carbonate/Sodium Bicarbonate Buffer):

In a 1000 ml round bottom flask, 50 g of crude 5-acetoxy-4-methyl-3,4-dihydro-2H-pyridine-1-carboxylic acid methyl ester was dissolved in 200 ml of methanol. To 300 ml water was added 30 g of sodium carbonate and 30 g sodium bicarbonate (pH=10). The aqueous buffer was added to the methanol solution. Methanol was added to the mixture until it stirred easily, and stirred at room temperature for 18 hours. The mixture was then concentrated to remove methanol. Water was added to the mixture to dissolve all salts. This was then extracted with ethyl acetate three times. The organic extracts were combined, dried over magnesium sulfate, filtered, and evaporated to furnish the crude compound 4-Methyl-3-oxo-piperidine-1-carboxylic acid methyl ester as oil, which was then purified as described below.

The resulting oil was split in half, and 26.9 g was run down a silica gel column using 350 ml of silica gel. The solvent was eluted as a gradient starting at 5% ethyl acetate in hexanes. The product was eluted with 10% ethyl acetate. Fractions showing pure product in TLC ($SiO_2$, Ethyl acetate/hexane 1:1) were combined and concentrated to afford 8.85 g (32% yield). Further fractions showing product with minor impurities in TLC were combined and concentrated. Additional material (3.2 g, 10%) slightly less pure was also isolated.

The remaining half of the crude product (26.9 g) was distilled in high vacuum. Fractions boiling at 99–100° C./1 mm was collected. Weight 12.1 g (yield, 41%). The material compared in TLC and NMR with the sample purified by chromatography but had minor non-polar impurities according to TLC ($SiO_2$, Ethyl acetate/hexane 1:1).

4-Methyl-3-methylamino-Diieridine-1-carboxylic acid methyl ester (Synthesized with Methylamine/Sodium Cyanoborohydride)

In a 100 ml round bottom flask, 4 g of impure 4-Methyl-3-oxo-piperidine-1-carboxylic acid methyl ester was dissolved in 20 ml methanol. To the stirring mixture was added 2M methylamine (25 ml in methanol solution). After 1 hour of stirring at room temperature, sodium cyanoborohydride, (0.7 g) was added, and stirred for 3 days. To quench the reaction, water (10 ml) was added with strong stirring, and then concentrated HCl was slowly added until the pH was strongly acidic (pH=~1), and remained acidic. After 2 hours, the mixture was concentrated, and the aqueous solution extracted twice with methylene chloride. The organic extracts were combined, dried over magnesium sulfate, filtered, and evaporated. The residue was run down a silica gel column with a gradient of 50% ethyl acetate in hexane, and ending with 100% methanol. Weight of material is 600 mg. NMR ($CDCl_3$) revealed that the desired compound 4-Methyl-3-methylamino-piperidine-1-carboxylic acid methyl ester was formed as a mixture of diastereomeric isomers. The ratio of the mixtures was approximately 1:1 from the splitting of the 4-methyl group. IR does show a C=O stretching for the carbamate.

4-Methyl-3-methylamino-piperidine-1-carboxylic acid methyl ester (Synthesized with Methylamine/Sodium Borohydride)

In a 50 ml round bottom flask, 2.0 g of the ketone 4-Methyl-3-oxo-piperidine-1-carboxylic acid methyl ester was dissolved in 6.0 ml of 2M methylamine in methanol. This solution was stirred for 1 hour, after which it was concentrated by rotary evaporation. In a separate 100 ml round bottom flask, 0.6 g sodium borohydride was added to 6 ml dry tetrahydrofuran under an argon atmosphere, and cooled in an ice bath. To the suspension, 3.6 ml glacial acetic acid was slowly added with stirring and continued cooling. The methylamine-ketone solution from above was diluted in absolute ethanol, and slowly added to the sodium borohydride solution with continued cooling in an ice bath. After addition was completed (ca. 1 hr), the mixture was allowed to warm to room temp. After 2 hours the flask was stored at 4° C. overnight. To the stirring solution was added 10 ml of water. After 20 minutes, concentrated hydrochloric acid was slowly added until the pH remained around 2. The mixture was then concentrated by rotary evaporation. The aqueous solution was made basic with sodium carbonate, and extracted three times with ethyl acetate. The organic layers were combined, dried over magnesium sulfate, filtered and concentrated by rotary evaporation. The oil was purified using a silica gel column with a solvent consisting of 1% ammonium hydroxide solution, 3% methanol in methylene chloride. Fractions showing the product were combined and solvent removed by rotary evaporation. Weight of product was 400 mg (18.5% yield). TLC compares with compound 4-Methyl-3-methylamino-piperidine-1-carboxylic acid methyl ester prepared by the other route.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a compound of formula (Ia):

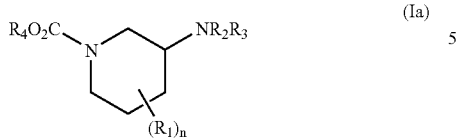

wherein $R_1$ is carboxy, cyano, deuterium, $(C_1-C_6)$alkyl, $(C_1-C_6)$alkoxy, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1C_6)$acyl, $((C_1-C_6)$alkyl$)_2$amino$(C_1-C_6)$acyl, $R_{15}R_{16}N$—CO—O—, $R_{15}R_{16}N$—CO—$(C_1-C_6)$alkyl, $(C_1-C_6)$alkyl-S(O)$_m$, $R_{15}R_{16}NS(O)_m$, $R_{15}R_{16}NS(O)_m$ $(C_1-C_6)$alkyl, $R_{15}S(O)_m$ $R_{16}N$, $R_{15}S(O)_m R_{16}N(C_1-C_6)$alkyl or a group of the formula (VII):

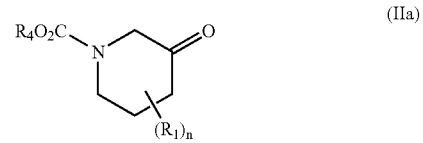

$R_2$ is hydrogen, $(C_1-C_6)$alkyl, $(C_1-C_6)$alkylsulfonyl, $(C_2-C_6)$alkenyl, or $(C_2C_6)$alkynyl wherein the alkyl, alkenyl and alkynyl groups are optionally substituted by deuterium, hydroxy, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R_2$ is $(C_3-C_{10})$cycloalkyl wherein the cycloalkyl group is optionally substituted by deuterium, hydroxy, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R_3$ is hydrogen, $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, halogen, trifluoromethyl, $(C_1-C_4)$alkoxy, $(C_1-C_6)$acyloxy, $(C_1-C_6)$alkylamino, $(C_1-C_6)$acylamino, $((C_1-C_6)$alkyl$)_2$amino, $(C_2-C_6)$alkenyl, $(C_2-C_6)$alkynyl, cyano, cyano$(C_1-C_6)$alkyl, trifluoromethyl$(C_1-C_6)$alkyl, nitro, or nitro$(C_1-C_6)$alkyl;

$R_4$ is $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, halogen, amino, trifluoromethyl, $(C_1-C_4)$alkoxy, $(C_1-C_6)$acyloxy, $(C_1-C_6)$alkylamino, $(C_1-C_6)$acylamino, $((C_1-C_6)$alkyl$)_2$amino, $(C_2-C_6)$alkenyl, $(C_2-C_6)$alkynyl, cyano, cyano$(C_1-C_6)$alkyl, trifluoromethyl$(C_1-C_6)$alkyl, nitro, or nitro$(C_1-C_6)$alkyl;

$R_6$, $R_7$, $R_8$, $R_9$, $R_{10}$ and $R_{11}$ are each independently hydrogen or $(C_1-C_6)$alkyl optionally substituted by deuterium, hydroxy, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino; $R_{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R_{15}R_{16}N$—CO—O—, $R_{15}R_{16}N$—CO—$(C_1-C_6)$alkyl, $R_{15}C(O)NH$, $R_{15}OC(O)NH$, $R_{15}NHC(O)NH$, $(C_1-C_6)$alkyl-S(O)$_m$, $(C_1-C_6)$alkyl-S(O)$_m$—$(C_1-C_6)$alkyl, $R_{15}R_{16}NS(O)_m$, $R_{15}R_{16}NS(O)_m$ $(C_1-C_6)$alkyl, $R_{15}S(O)_m$ $R_{16}N$, or $R_{15}S(O)_m R_{16}N(C_1-C_6)$alkyl;

$R_{15}$ and $R_{16}$ are each independently hydrogen or $(C_1-C_6)$alkyl;

X is $S(O)_p$, oxygen, carbonyl or —C(═N-cyano)-;

Y is $S(O)_p$ or carbonyl;

Z is $S(O)_p$, carbonyl, C(O)O—, or C(O)NR—;

a is 0, 1, 2, 3 or 4;

b, c, e, f and g are each independently 0 or 1;

d is 0, 1, 2, or 3;

m is 0, 1 or 2;

n is 1, 2, 3, or 4;

p is 0, 1 or 2; and wherein the method comprises reacting $NHR_2R_3$, $N(CH_3)R_2H$, or $N(CH_2CH_3)R_2H$ with a compound of formula (IIa):

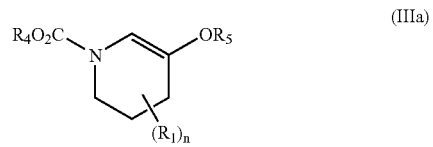

and reducing the compound so formed with a reducing agent.

2. The method of claim 1, wherein the method further comprises formation of the compound of the formula (IIa) by reacting a compound having the formula $R_4OH$, water, or $R_4NH_2$ and a compound of the formula (IIIa):

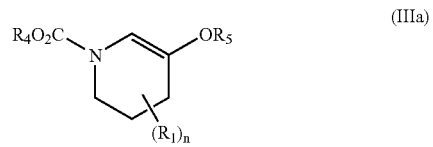

wherein $R_5$ is $CO(C_1-C_6)$alkyl.

3. The method of claim 2, wherein the method further comprises formation of the compound of the formula (IIIa) by heating a compound having the formula (IVa):

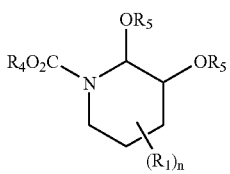

(IVa)

with a compound having the formula $(C_1-C_6)$alkyl-$(C=O)-O-(C=O)-(C_1-C_6)$alkyl.

4. The method of claim 3, wherein the method further comprises formation of the compound of the formula (IVa) by oxidizing a compound having the formula (Va):

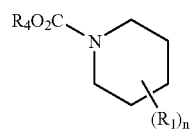

(Va)

under oxidizing conditions.

5. The method of claim 4, wherein the method further comprises formation of the compound of the formula (Va) by reacting a compound having the formula $WCO_2R_4$ and a compound having the formula (Via):

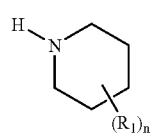

(Via)

wherein W is halogen.

6. The method of claim 4, wherein the oxidizing conditions are an electrochemical oxidation.

7. A method of making a compound having the formula (Ib):

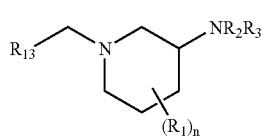

(Ib)

wherein $R_1$ is carboxy, amino, deuterium, hydroxy, $(C_1-C_6)$alkyl, $(C_1-C_6)$alkoxy, $(C_1-C_6)$alkylamino, amino$(C_1-C_6)$alkyl, $(C_2-C_6)$alkenyl, $(C_2-C_6)$ alkynyl, $(C_1-C_6)$alkylamino, amino$(C_1-C_6)$alkyl, hydroxy $(C_1-C_6)$alkyl, $(C_1-C_6)$alkoxy$(C_1-C_6)$alkyl, nitro, nitro $(C_1-C_6)$alkyl, trifluoromethyl, trifluoromethyl$(C_1-C_6)$ alkyl, $(C_1-C_6)$alkyl-$S(O)_m$, $R_{15}R_{16}NS(O)_m$, $R_{15}R_{16}NS$ $(O)_m$ $(C_1-C_6)$alkyl, $R_{15}S(O)_m$ $R_{16}N$, $R_{15}S(O)_m R_{16}N$ $(C_1-C_6)$alkyl or a group of the formula (VII):

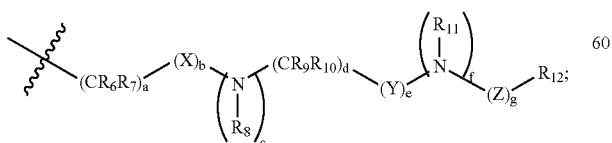

(VII)

$R_2$ is hydrogen, $(C_1-C_6)$alkyl, $(C_1-C_6)$alkylsulfonyl, $(C_2-C_6)$alkenyl, or $(C_2C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$alkylamino, $((C_1-C_6)$alkyl$)_2$amino, nitro, $(C_2-C_6)$alkenyl, or $(C_2-C_6)$alkynyl; or $R_2$ is $(C_3-C_{10})$cycloalkyl wherein the cycloalkyl group is optionally substituted by deuterium, hydroxy, amino, trifluoromethyl, $(C_1-C_6)$alkylamino, $((C_1-C_6)$alkyl$)_2$amino, trifluoromethyl$(C_1-C_6)$alkyl, nitro, or nitro $(C_1-C_6)$alkyl;

$R_3$ is hydrogen, $(C_1-C_6)$alkyl, $(C_3-C_{10})$cycloalkyl, $(C_2-C_6)$alkenyl, or $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$alkenylamino $((C_1-C_6)$alkyl$)_2$amino, $(C_2-C_6)$alkenyl, $(C_2-C_6)$alkynyl, trifluoromethyl$(C_1-C_6)$alkyl, nitro, or nitro$(C_1-C_6)$ alkyl;

$R_6$, $R_7$, $R_8$, $R_9$, $R_{10}$ and $R_{11}$ are each independently hydrogen or $(C_1-C_6)$alkyl optionally substituted by deuterium, hydroxy, amino, trifluoromethyl, $(C_1-C_6)$ alkylamino, $((C_1-C_6)$alkyl$)_2$amino, trifluoromethyl $(C_1-C_6)$alkyl, nitro, or nitro$(C_1-C_6)$alkyl; $R_{12}$ is carboxy, amino, deuterium, hydroxy, trifluoromethyl, $(C_1-C_6)$alkyl, trifluoromethyl$(C_1-C_6)$alkyl, $(C_1-C_6)$ alkoxy, $(C_1-C_6)$alkylamino, $((C_1-C_6)$alkyl$)_2$ amino, amino$(C_1-C_6)$alkyl, $(C_2-C_6)$alkenyl, $(C_2-C_6)$ alkynyl, $(C_1-C_6)$alkylamino, hydroxy$(C_1-C_6)$alkyl, $(C_1-C_6)$ alkoxy$(C_1-C_6)$alkyl, nitro, nitro$(C_1-C_6)$alkyl, trifluoromethyl, trifluoromethyl$(C_1-C_6)$alkyl, $(C_1-C_6)$ alkyl-$S(O)_m$, $(C_1-C_6)$alkyl-$S(O)_m-(C_1-C_6)$alkyl, $R_{15}R_{16}NS(O)_m$, $R_{15}R_{16}NS(O)_m$ $(C_1-C_6)$alkyl, or $R_{15}S$ $(O)_m$ $R_{16}N$, or $R_{15}S(O)_m R_{16}N(C_1-C_6)$alkyl;

$R_{13}$ is $(C_2-C_6)$alkenyl, $(C_2-C_6)$alkynyl, $(C_6-C_{10})$aryl, $(C_1-C_6)$carboalkoxy, $(C_5-C_9)$heteroaryl, $(C_6-C_{10})$aryl $(C_1-C_6)$alkyl, or $(C_5-C_9)$heteroaryl$(C_1-C_6)$alkyl wherein the $R_{13}$ group is optionally substituted by deuterium, hydroxy, amino, trifluoromethyl, $(C_1-C_6)$ alkyl, $(C_1-C_4)$alkoxy, $(C_1-C_6)$alkylamino, $((C_1-C_6)$ alkyl$)_2$amino, $(C_2-C_6)$alkenyl, $(C_2-C_6)$alkynyl, trifluoromethyl$(C_1-C_6)$alkyl, nitro, or nitro$(C_1-C_6)$ alkyl;

$R_{15}$ and $R_{16}$ are each independently hydrogen or $(C_1-C_6)$ alkyl;

X is $S(O)_p$;
Y is $S(O)_p$;
Z is $S(O)_p$;
a is 0, 1, 2, 3 or 4;
b, c, e, f and g are each independently 0 or 1;
d is 0, 1, 2, or 3;
m is 0, 1 or 2;
n is 1, 2, 3, or 4;
p is 0, 1 or 2; and wherein the method comprises reducing a compound of formula (IIb):

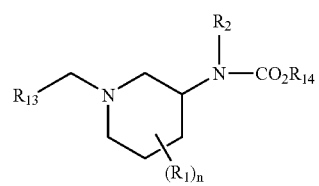

(IIb)

with a reducing agent, wherein $R_{14}$ is $(C_1-C_6)$alkyl, $(C_3-C_{10})$cycloalkyl, $(C_2-C_6)$alkenyl, or $(C_2-C_6)$ alkynyl wherein the alkyl, alkenyl and alkynyl groups are optionally substituted by deuterium, hydroxy, halogen, amino, trifluoromethyl, $(C_1-C_4)$alkoxy, $(C_1-C_6)$alkylamino, $((C_1-C_6)$alkyl$)_2$amino, $(C_2-C_6)$alkenyl, $(C_2-C_6)$alkynyl, trifluoromethyl$(C_1-C_6)$alkyl, nitro, or nitro$(C_1-C_6)$alkyl.

8. The method of claim 7, wherein the method further comprises formation of the compound of the formula (IIb) by reacting a compound having the formula (IIIb):

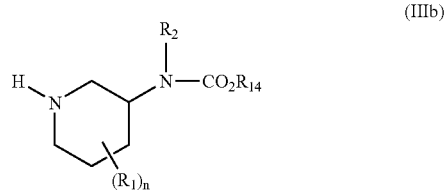

(IIIb)

with an aldehyde of formula $R_{13}$—(C=O)—H and reducing the compound so formed with a reducing agent.

9. The method of claim 8, wherein the method further comprises formation of the compound of the formula (IIIb) by hydrogenating a compound having the formula (IVb):

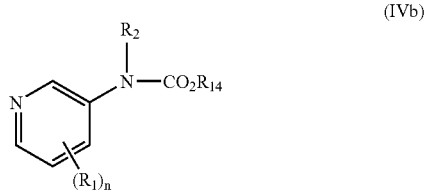

(IVb)

in the presence of a catalyst.

10. The method of claim 9, wherein the method further comprises formation of the compound of the formula (IVb) by reacting a compound having the formula (Vb):

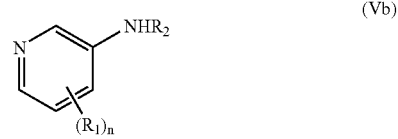

(Vb)

with $(R_{14}$—O—(C=O)$)_2$O or $R_{14}$—O—(C=O)—X wherein X is halo.

11. The method of claim 1, wherein the compound of formula (Ia) has the relative stereochemistry of formula (Ia-1):

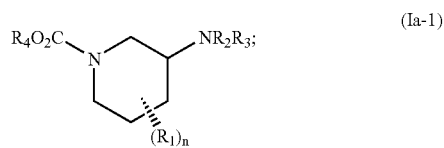

(Ia-1)

$R_1$ is $(C_1-C_6)$alkyl; n is one; $R_2$ and $R_3$ are each hydrogen or $(C_1-C_6)$alkyl; and $R_4$ is $(C_1-C_6)$alkyl.

12. The method of claim 7, wherein the compound of formula (Ib) has the relative stereochemistry of formula (Ib-1)

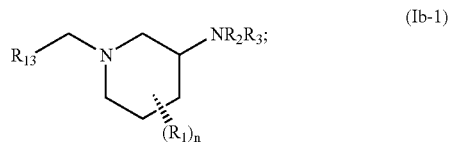

(Ib-1)

$R_1$ is $(C_1-C_6)$alkyl; n is one; $R_2$ and $R_3$ are each hydrogen or $(C_1-C_6)$alkyl; and $R_{13}$ is $(C_6-C_{10})$aryl.

13. The method of claim 1, wherein the reducing agent is a borohydride.

14. The method of claim 7, wherein the reducing agent is lithium aluminum hydride.

15. The method of claim 9, wherein the catalyst is Rh/alumina or Rh/C.

* * * * *

UNITED STATES PATENT AND TRADEMARK OFFICE
CERTIFICATE OF CORRECTION

PATENT NO. : 7,084,277 B2
APPLICATION NO. : 10/717958
DATED : August 1, 2006
INVENTOR(S) : David H.B. Ripin It is certified that error appears in the above-identified patent and that said Letters Patent is hereby corrected as shown below:

Column 1, line 14, please replace "3-amino-piperadine" with --3-amino-piperidine--.

Column 26, line 15, please replace " 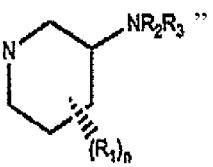 " with

-- 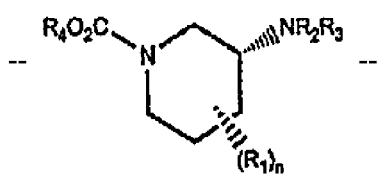 --

Column 26, line 30, please replace " 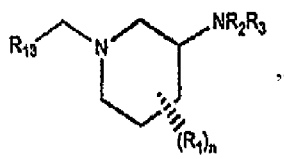 " with

-- 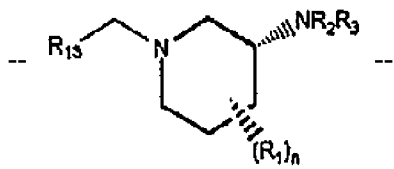 --

Signed and Sealed this

Sixteenth Day of January, 2007

JON W. DUDAS
*Director of the United States Patent and Trademark Office*